(12) United States Patent
Cionni

(10) Patent No.: US 7,083,591 B2
(45) Date of Patent: Aug. 1, 2006

(54) SURGE-FLOW REGULATOR FOR USE IN OPHTHALMIC SURGICAL ASPIRATION

(76) Inventor: Robert J. Cionni, 11425 Grandstone La., Cincinnati, OH (US) 45249

( * ) Notice: Subject to any disclaimer, the term of this patent is extended or adjusted under 35 U.S.C. 154(b) by 304 days.

(21) Appl. No.: 10/363,106
(22) PCT Filed: Sep. 7, 2001
(86) PCT No.: PCT/US01/28203

§ 371 (c)(1),
(2), (4) Date: Feb. 28, 2003

(87) PCT Pub. No.: WO02/19896

PCT Pub. Date: Mar. 14, 2002

(65) Prior Publication Data
US 2004/0077993 A1   Apr. 22, 2004

Related U.S. Application Data

(60) Provisional application No. 60/230,779, filed on Sep. 7, 2000.

(51) Int. Cl.
*A61M 1/00* (2006.01)
*A61B 17/20* (2006.01)
*A61B 18/18* (2006.01)
*A61B 17/22* (2006.01)

(52) U.S. Cl. .............................. 604/31; 604/22; 604/34; 604/35; 604/151; 606/6; 606/107

(58) Field of Classification Search .................. 604/14, 604/19, 22, 27, 28, 30, 35, 48, 65, 67, 113, 604/131, 151, 153, 246, 247, 289, 290, 291, 604/294, 31, 34; 606/4, 5, 6, 107, 127, 128; 600/401, 402; 607/53, 54
See application file for complete search history.

(56) References Cited

U.S. PATENT DOCUMENTS

| 4,702,733 | A | * | 10/1987 | Wright et al. ................. 604/34 |
| 4,787,889 | A | | 11/1988 | Steppe et al. ................. 604/22 |
| 4,808,154 | A | | 2/1989 | Freeman ...................... 604/22 |
| 4,816,017 | A | | 3/1989 | Hood et al. ................... 604/22 |
| 4,921,477 | A | | 5/1990 | Davis .......................... 604/22 |
| 4,983,160 | A | | 1/1991 | Steppe et al. ................. 604/22 |

(Continued)

OTHER PUBLICATIONS

PCT, *International Search Report*, International Application No. PCT/US01/28203, ISA/US, Filed Sep. 7, 2001 (2 pages).

Primary Examiner—Sharon Kennedy
Assistant Examiner—Mark K Han
(74) Attorney, Agent, or Firm—Wood, Herron & Evans, LLP

(57) ABSTRACT

A surge-flow regulator (36) for use with an ophthalmic surgical instrument (12) having an infusion line (20) adapted to irrigate a surgical site with fluid and an aspiration line (24) adapted to carry the fluid and particles of lenticular debris away from the surgical site. The surge-flow regulator (36) includes a flow limiting device (40) that is placed in fluid communication with the aspiration line (24) to control surge-flow of the aspirated fluid and lenticular debris through the aspiration line (24). The lenticular debris carried in the aspiration line (24) is processed into smaller particles before the fluid and debris are introduced to the flow limiting device (40).

26 Claims, 5 Drawing Sheets

U.S. PATENT DOCUMENTS

| | | | |
|---|---|---|---|
| 5,084,009 A | 1/1992 | Mackool | 604/22 |
| 5,106,367 A | 4/1992 | Ureche et al. | 604/30 |
| 5,167,620 A | 12/1992 | Ureche et al. | 604/28 |
| 5,188,589 A | 2/1993 | Wypych et al. | 604/22 |
| 5,476,448 A | 12/1995 | Urich | 604/22 |
| 5,725,495 A | 3/1998 | Strukel et al. | 604/44 |
| 6,039,715 A | 3/2000 | Mackool | 604/272 |
| 6,042,586 A | 3/2000 | Kawano et al. | 606/107 |
| 6,258,053 B1 | 7/2001 | Mackool | 604/22 |
| 6,299,591 B1 | 10/2001 | Banko | 604/22 |
| 6,599,271 B1 | 7/2003 | Easley | 604/119 |

* cited by examiner

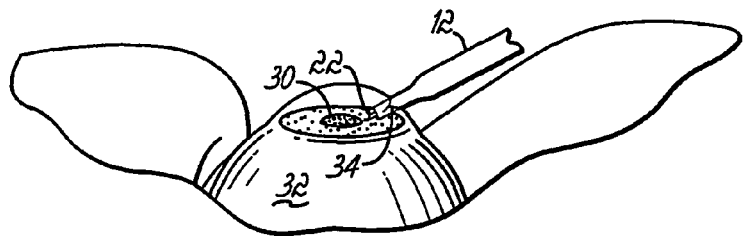
FIG. 2
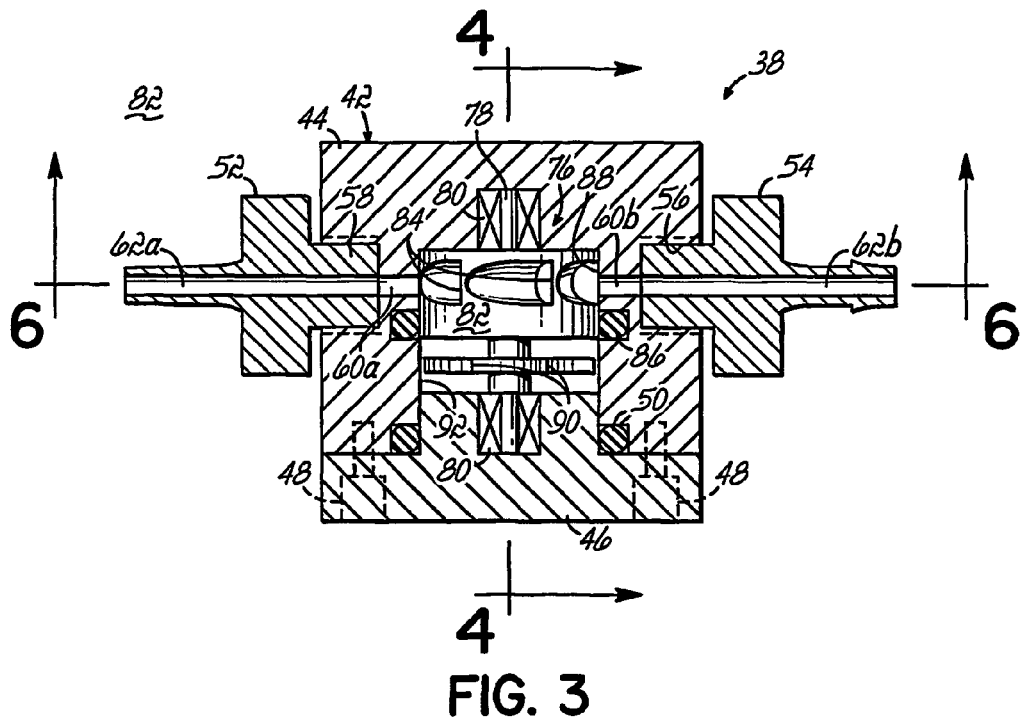
FIG. 3
FIG. 4

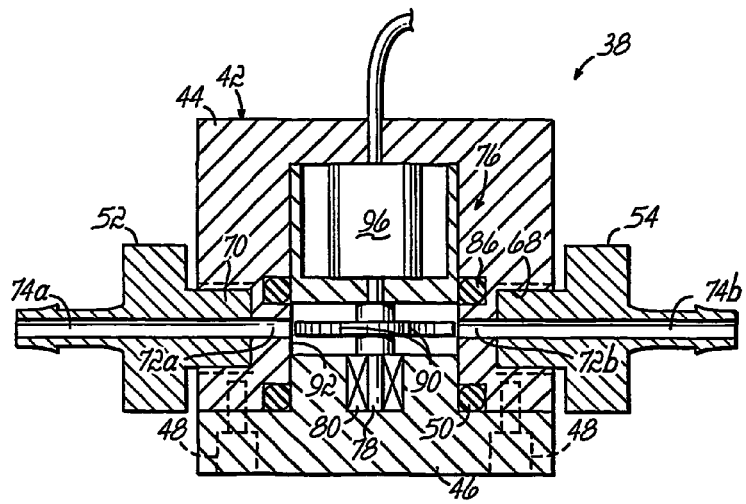
FIG. 7
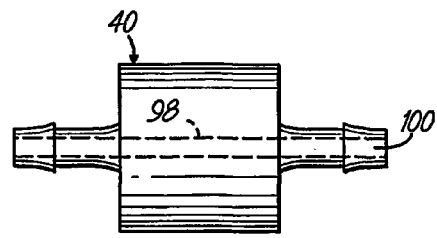
FIG. 8
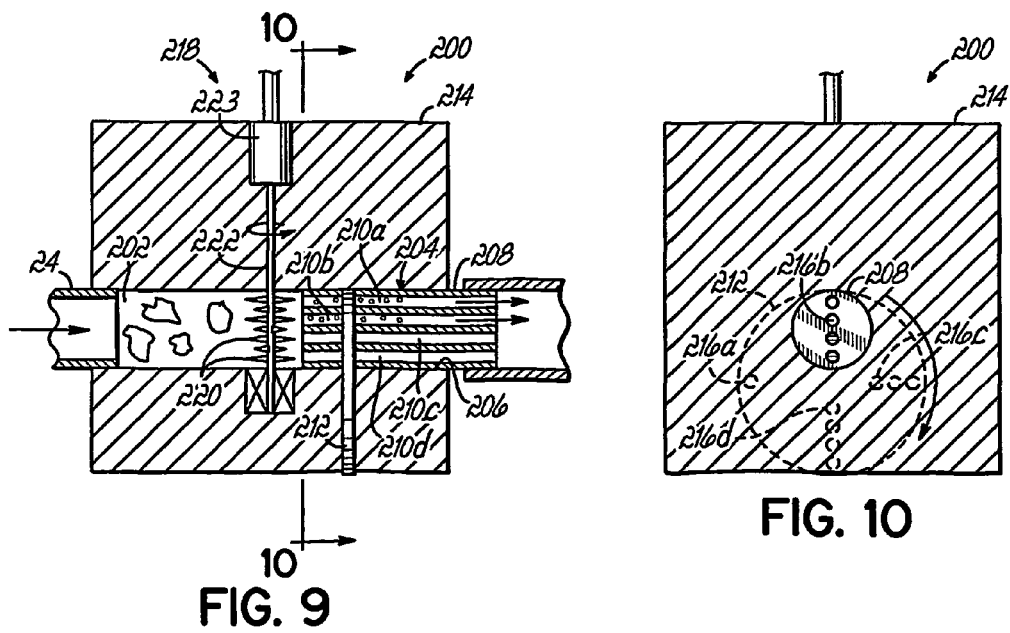
FIG. 9
FIG. 10

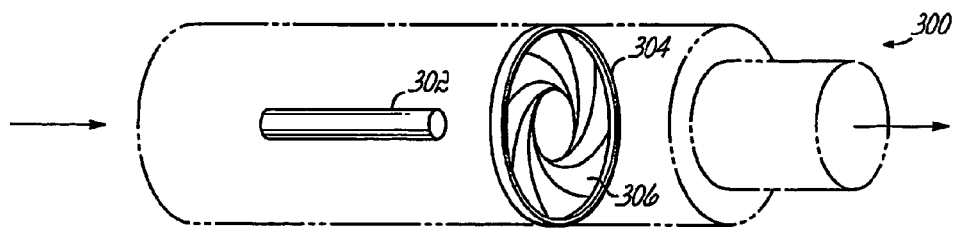
FIG. 11
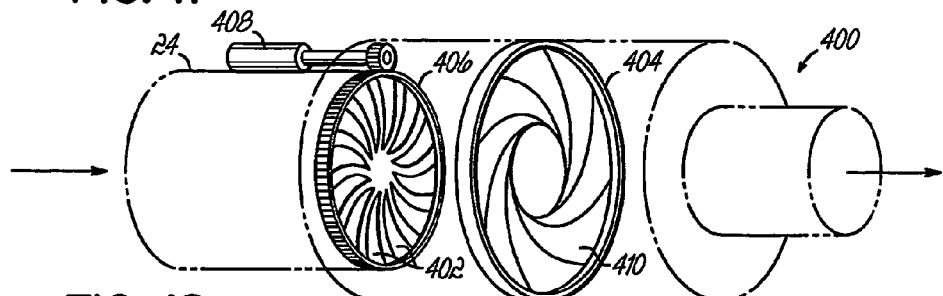
FIG. 12
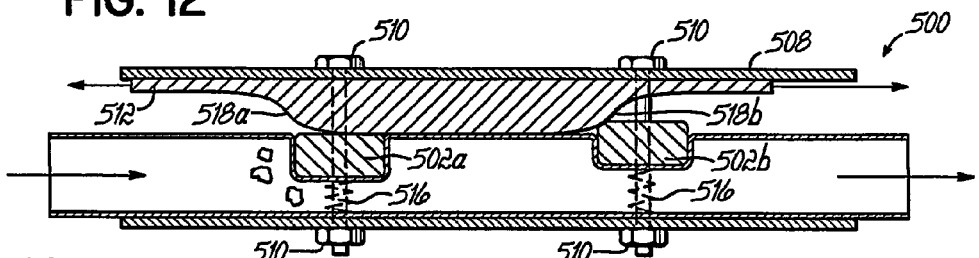
FIG. 13
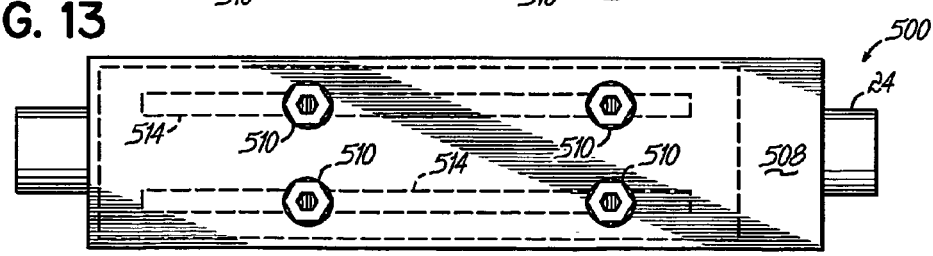
FIG. 14
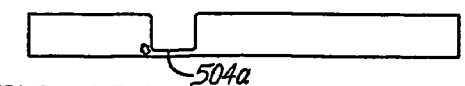
FIG. 15A
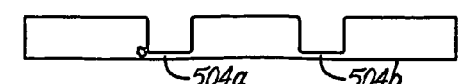
FIG. 15B
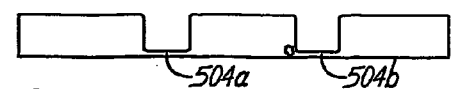
FIG. 15D
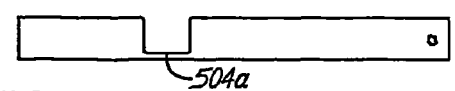
FIG. 15E
FIG. 15C

SURGE-FLOW REGULATOR FOR USE IN OPHTHALMIC SURGICAL ASPIRATION

This application claims the benefit of Provisional Application No. 60/230,779, filed Sep. 7, 2000.

FIELD OF THE INVENTION

The present invention relates generally to ophthalmic surgical instruments and, more particularly, to a phacoemulsification system for irrigating and aspirating a human eye during an ophthalmic surgical procedure.

BACKGROUND OF THE INVENTION

Phacoemulsification is a well-known process that refers to the use of a phacoemulsification machine that generates ultrasonic sound waves at the tip of a handpiece. phacoemulsification machines are particularly useful in cataract surgery, for example, where it is necessary to remove a cataract lens from an eye. The tip is placed into the eye and specifically against the lens or cataract of the eye where the ultrasonic energy emulsifies the lens. The tip is hollow and emulsified pieces of the cataract are aspirated into an aspiration port formed at an end of the tip for removal from the eye. The aspirated cataract material flows through the tip, through channels within the handpiece and into an aspiration line connected to the phacoemulsification machine while fluid flows into the eye through an infusion line and an infusion sleeve formed around the tip to maintain the eye's pressure and shape.

Aspiration is driven by pumps housed within the phacoemulsification machine and infusion is typically generated by gravity. The fluid infused into the eye through the infusion sleeve also serves to suspend particles of lenticular debris within the infused fluid and the suspension is then aspirated through the aspiration line back to the phacoemulsification machine where it is collected in a receptacle. The flow created in the aspiration line generates a vacuum or negative pressure in the aspiration line and at the handpiece tip. The vacuum holds the lens material against the aspiration port of the tip where the material is emulsified.

The stronger the vacuum force is that holds the material against the aspiration port, i.e., "holdability", the more efficient emulsification becomes. Additionally, increasing holdability allows the surgeon to manipulate lens material within the handpiece tip more easily. Holdability increases with vacuum level and aspiration port size. Therefore, higher vacuum levels and larger aspiration ports lead to more efficient phacoemulsification. However, these parameters also risk sudden collapse of the anterior chamber of the eye as fluid rapidly rushes into the aspiration port due to the large aspiration port area and the high vacuum.

For example, during aspiration of the lenticular debris, the handpiece tip often becomes occluded with this debris. When it does, the vacuum level within the aspiration line builds to a high level. Eventually, the ultrasonic sound waves at the tip emulsify the debris, freeing the occlusion at the tip and resulting in an "occlusion break". Fluid then rapidly rushes into the aspiration port and aspiration line to satisfy the high vacuum built up in the tip and the aspiration line. This can create negative pressure in the anterior chamber relative to the posterior segment of the eye. When this occurs, the anterior chamber can collapse or the posterior capsule can shift anteriorly, both being undesirable during intraocular surgery, perhaps resulting in complications such as posterior capsule rupture.

To reduce the potential surge inflow of fluid in the aspiration line resulting from an occlusion break at the tip, emulsification tips have been manufactured in the past with a narrow lumen within the shaft of the tip that allows the surgeon to increase vacuum levels while limiting the sudden inflow of fluid in the aspiration line following an occlusion break. However, in these tip designs, the narrow portion of the lumen often becomes occluded with debris resulting in a complete loss of negative pressure or holdability at the aspiration port of the tip. The occlusion can be broken by refluxing fluid, prolonged application of ultrasonic energy or sometimes by increasing the vacuum level in the aspiration line. However, these techniques either increase the risk of complications, such as thermal injury to ocular tissues, or decrease efficiency of the emulsification surgical procedure. Additionally, these tip designs tend to have thinner walls than standard tips and are relatively fragile and more prone to breakage.

Thus, there is a need for a phacoemulsification system that reduces the danger of sudden post occlusion surge inflow of fluid within the aspiration line following an occlusion break. There is also a need for a phacoemulsification system that minimizes occlusions at the narrow lumen that can lead to a complete loss of holdability at the handpiece tip. There is yet another need for a phacoemulsification machine that improves holdability of the handpiece tip while minimizing breakage of the tip. There is still also a need for a phacoemulsification system that minimizes the risk of injury to the human eye during a phacoemulsification surgical procedure.

SUMMARY OF THE INVENTION

The present invention overcomes the foregoing and other shortcomings and drawbacks of phacoemulsification systems and methods of emulsifying and aspirating lenticular debris heretofore known. While the invention will be described in connection with certain embodiments, it will be understood that the invention is not limited to these embodiments. On the contrary, the invention includes all alternatives, modifications and equivalents as may be included within the spirit and scope of the present invention.

According to the principles of the present invention, a surge-flow regulator is provided for use with an ophthalmic surgical instrument having an elongated handpiece containing an infusion line adapted to irrigate a surgical site with a fluid and an emulsification tip in fluid communication with an aspiration line adapted to carry the fluid and particles of emulsified lenticular debris away from the surgical site.

In accordance with one aspect of the present invention, the surge-flow regulator includes a flow limiting device adapted to be placed in fluid communication with the aspiration line and positioned remote from the emulsification tip. Alternatively, the flow limiting device is positioned remote from the emulsification tip and the handpiece. The flow limiting device defines a fluid passage having an inner diameter that is less than an inner diameter of the aspiration line to limit post occlusion surge inflow of fluid within the aspiration line following an occlusion break at the tip. Remote location of the flow limiting device from the emulsification tip minimizes the risk of injury to the human eye caused by occlusion of the narrow lumen that requires refluxing fluid, prolonged application of ultrasonic energy or an increased vacuum level in the aspiration line to break it up. Additionally, the flow limiting device allows the surgeon to use a standard tip which is less susceptible to breakage and the surgeon is able to chose the lumen size of the tip based on his or her surgical technique.

The flow limiting device may comprise a lumen adapted to be placed in fluid communication with the aspiration line. The lumen is interchangeable with a lumen having a different inner diameter to allow the surgeon to tailor the surge-flow regulator to the surgeon's surgical technique and the particular patient. Alternatively, the flow limiting device may comprise a lumen that defines multiple fluid passages through the lumen. A rotatable occluding device is provided to allow the surgeon to selectively occlud the fluid passages of the lumen to obtain higher or lower aspiration rates. In another embodiment, the lumen comprises an adjustable iris member that defines a fluid passage having a variable inner diameter.

In yet another embodiment, the flow limiting device is mounted externally to the aspiration line and includes a pair of compression members adapted to apply external pressures to the aspiration line at spaced apart locations that define a pair of spaced apart fluid passages within the aspiration line. The spaced apart fluid passages within the aspiration line have respective diameters that change upon changing the external pressures applied to the aspiration line by the pair of compression members. The aspiration line has a reduced inner diameter at either one of the fluid passages, or at both fluid passages, so that the reduced diameter of the aspiration line limits post occlusion surge inflow of fluid in the aspiration line following an occlusion break at the tip yet debris is allowed to pass through the aspiration line to the receptacle of the phacoemulsification machine.

In accordance with another aspect of the present invention, the surge-flow regulator includes a processor placed in fluid communication with the aspiration line upstream of the flow limiting device. The processor is adapted to process the particles of lenticular debris carried in the aspiration line into smaller particles before the fluid and particles are introduced to the flow limiting device. This reduces the chance of clogging the flow limiting device with lenticular debris that may otherwise occlude the flow limiting device and cause a sudden inflow of fluid through the aspiration line during an occlusion break.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 2 is a side elevational view of a human eye undergoing a ophthalmic surgical procedure using the phacoemulsification system illustrated in FIG. 1;

FIG. 3 is cross sectional view of a processor component of the surge-flow regulator illustrated in FIG. 1 taken along line 3—3 of FIG. 1;

FIG. 4 is a cross sectional view of the processor component of the surge-flow regulator illustrated in FIG. 1 taken along line 4—4 of FIG. 3;

FIG. 7 is a cross sectional view of a processor component of the surge-flow regulator in accordance with an alternative embodiment of the present invention;

FIG. 8 is a side elevational view of a flow limiting component of the surge-flow regulator illustrated in FIG. 1;

FIG. 9 is a cross sectional view of a surge-flow regulator in accordance with an alternative second embodiment of the present invention;

FIG. 10 is a cross sectional view of the surge-flow regulator illustrated in FIG. 9 taken along line 10—10 of FIG. 9;

FIG. 11 is a perspective view of a surge-flow regulator in accordance with an alternative third embodiment of the present invention;

FIG. 12 is a view similar to FIG. 11 illustrating a surge-flow regulator in accordance with an alternative fourth embodiment of the present invention;

FIG. 13 is a side elevational view, partially in cross section, illustrating a surge-flow regulator in accordance with an alternative fifth embodiment of the present invention;

FIG. 14 is a top plan view of the surge-flow regulator illustrated in FIG. 13; and FIGS. 15A–15E are functional diagrams showing operation of the surge-flow regulator illustrated in FIG. 13.

DETAILED DESCRIPTION OF SPECIFIC EMBODIMENTS

Figure 1:
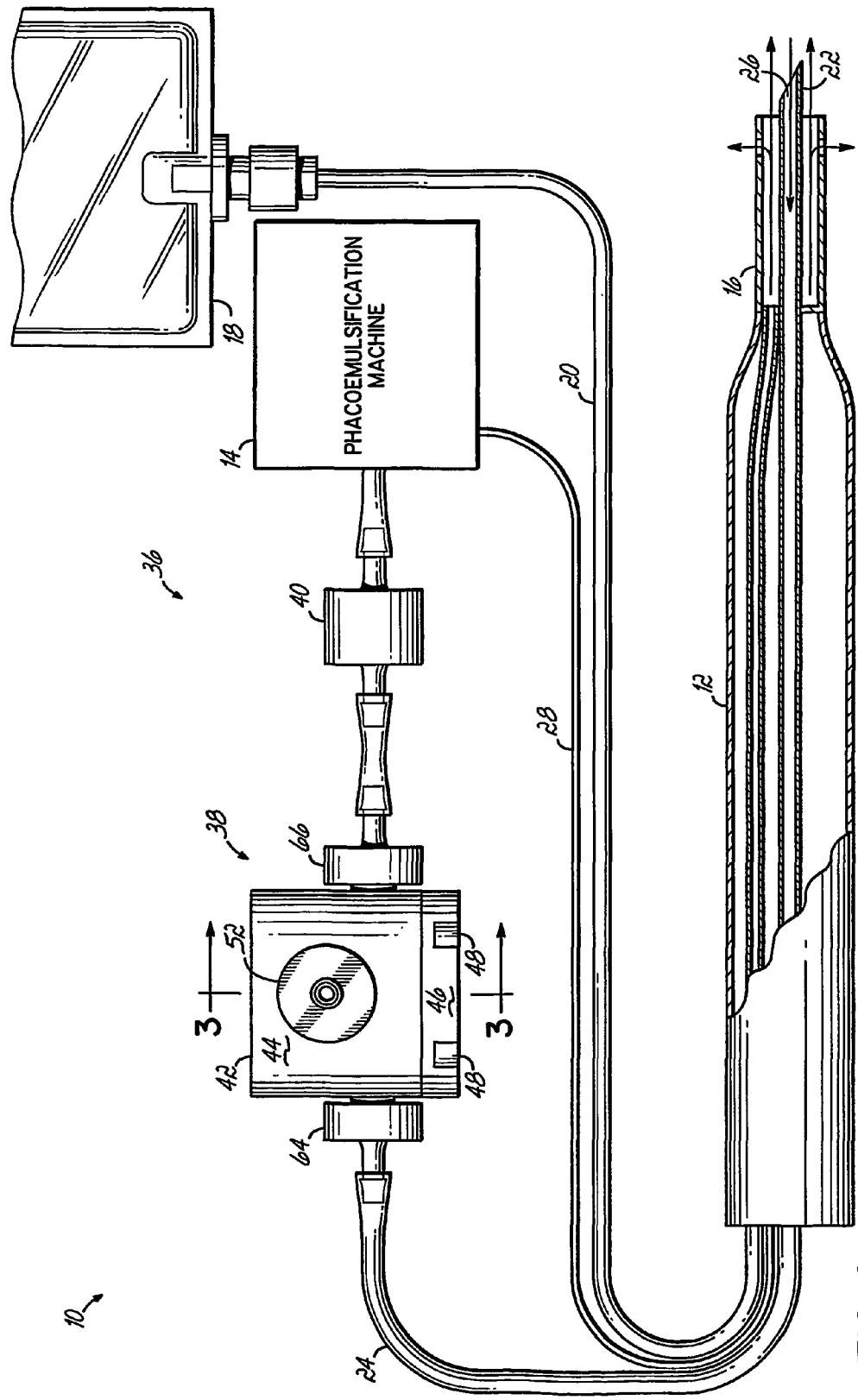
FIG. 1 is a schematic view of a phacoemulsification system incorporating a surge-flow regulator in accordance with one embodiment of the present invention.

Referring now to FIG. 1, a phacoemulsification system 10 in accordance with one embodiment of the present invention is shown including a phacoemulsification handpiece 12 connected to a phacoemulsification machine 14. Handpiece 12 and machine 14 are conventional phacoemulsification instruments and operate in a manner well known to those of ordinary skill in the art.

Briefly, the phacoemulsification handpiece 12 includes an infusion sleeve 16 connected to a fluid supply 18, such as saline or other ophthalmic surgical fluid, via infusion line 20. The fluid supply 18 delivers fluid under pressure to the infusion sleeve 16 of handpiece 12 for irrigating a surgical site as will be described in greater detail below. The handpiece 12 also includes an emulsification tip 22 mounted coaxially within the irrigation sleeve 16 that is connected to the phacoemulsification machine 14 via an aspiration line 24. The aspiration line 24 is connected to a vacuum pump (not shown) mounted within the phacoemulsification machine 14 for providing a negative pressure or vacuum at an aspiration port 26 formed at a distal end of the tip 22. The tip 22 is electrically coupled to the phacoemulsification machine 14 via power cord 28 so that the tip 22 is made to vibrate with an ultrasound frequency of 25,000 to 100,000 cycles per second or higher as known by those of ordinary skill in the art.

Phacoemulsification system 10 is particularly useful in cataract surgery, for example, where it is necessary to remove a cataract lens from an eye. As shown in FIG. 2, the cataract lens 30 is removed from the eye 32 by emulsifying the lens 30 with the emulsification tip 22 of the handpiece 12 and aspirating the lenticular debris generated during the emulsification procedure via aspiration line 24. Typically, an incision 34 is made in the corneal rim of the eye 32 and the emulsification tip 22 and surrounding infusion sleeve 16 are inserted into the eye 32 through the incision 34. The emulsification tip 22, vibrating at an ultrasonic frequency, is manipulated into contact with the cataract lens 30 and the high frequency vibrating tip 22 serves to emulsify the cataract lens 30 within the lens capsular bag. The fluid infused into the eye 32 through the infusion sleeve 16 serves to maintain the eye's pressure and shape and also to suspend particles of lenticular debris within the infused fluid and the suspension is then aspirated through the aspiration line 24 back to the phacoemulsification machine 14 where it is collected in a receptacle (not shown).

In accordance with one aspect of the present invention, as shown in FIG. 1, a surge-flow regulator 36 is placed in fluid communication with the aspiration line 24 between the handpiece 12 and the phacoemulsification machine 14 to reduce the danger of sudden post occlusion surge inflow of fluid within the aspiration line 24 following an occlusion break at the tip 22. The surge-flow regulator 36 comprises in one embodiment a processor 38 placed in fluid communication with the aspiration line 24 and a flow limiting device 40 positioned downstream of the processor 38 and also placed in fluid communication with the aspiration line 24.

As will be described in detail below, the processor 38, which may take many forms understood by those skilled in the art, is adapted to process the particles of lenticular debris carried in the aspiration line 24 into smaller particles before the fluid and particles are introduced to the flow limiting device 40. As used herein, the terms "processor" and "process" are intended to include any device or process that is capable of reducing the size of the lenticular debris particles carried in the aspiration line 24. For example, the "processor" may comprise, without limitation, a compressor, grinder, driller, crusher, shredder, emulsifier or any other device or process that is capable of reducing the size of the lenticular debris particles carried in the aspiration line 24 following the emulsification procedure. While the present invention will be described by way of example in use in an emulsification surgical procedure, it will be appreciated that the present invention is not limited to emulsification procedures but is readily adaptable to many surgical procedures that produce debris that must be aspirated through an aspiration line. While the surge-flow regulator 36 is shown separate from the handpiece 12, it is contemplated that one or both of the processor 38 and the flow limiting device 40 may be supported by or mounted within the handpiece 12 in an alternative embodiment (not shown) without departing from the spirit and scope of the present invention.

As will also be described in detail below, the flow limiting device 40 provides one or more fluid passages having an inner diameter that is less than the inner diameter of the aspiration line 24 to limit post occlusion surge inflow of fluid within the aspiration line 24 following an occlusion break at the tip 22. The flow limiting device 40 may be positioned separate from the processor 38 and connected to the processor 38 through a portion of the aspiration line 24 as shown in FIG. 1 or, alternatively, the flow limiting device 40 may be formed integrally as part of the processor 38 or rigidly connected to the processor 38 through a threaded connection, glue, welding or any other fastening structure or process.

Figure 5:
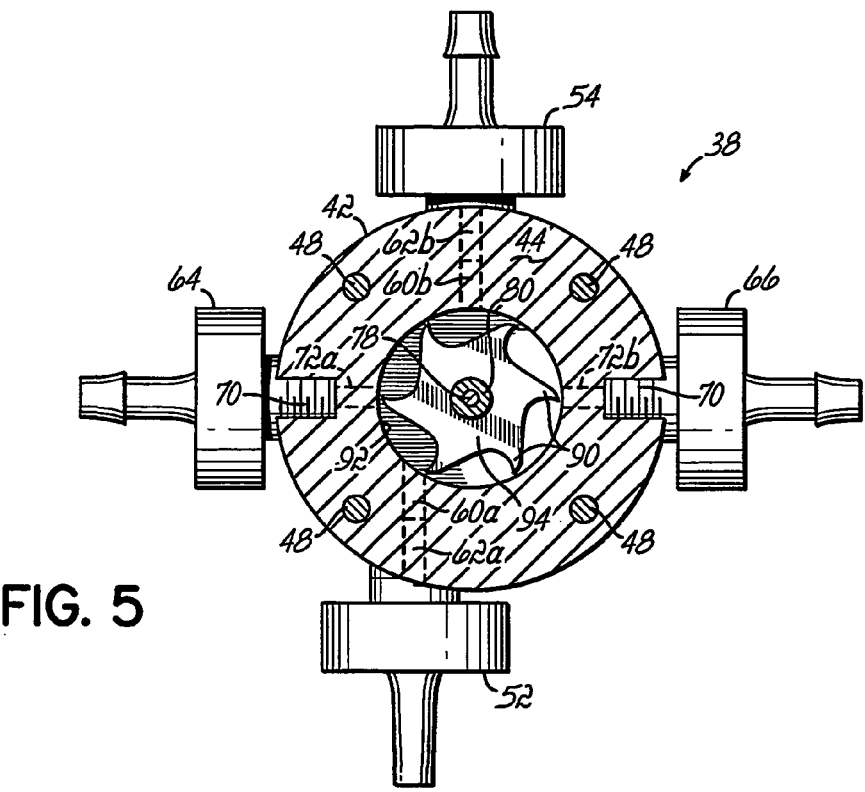
FIG. 5 is a cross sectional view of the processor component of the surge-flow regulator illustrated in FIG. 1 taken along line 5—5 of FIG. 4.
Figure 6:
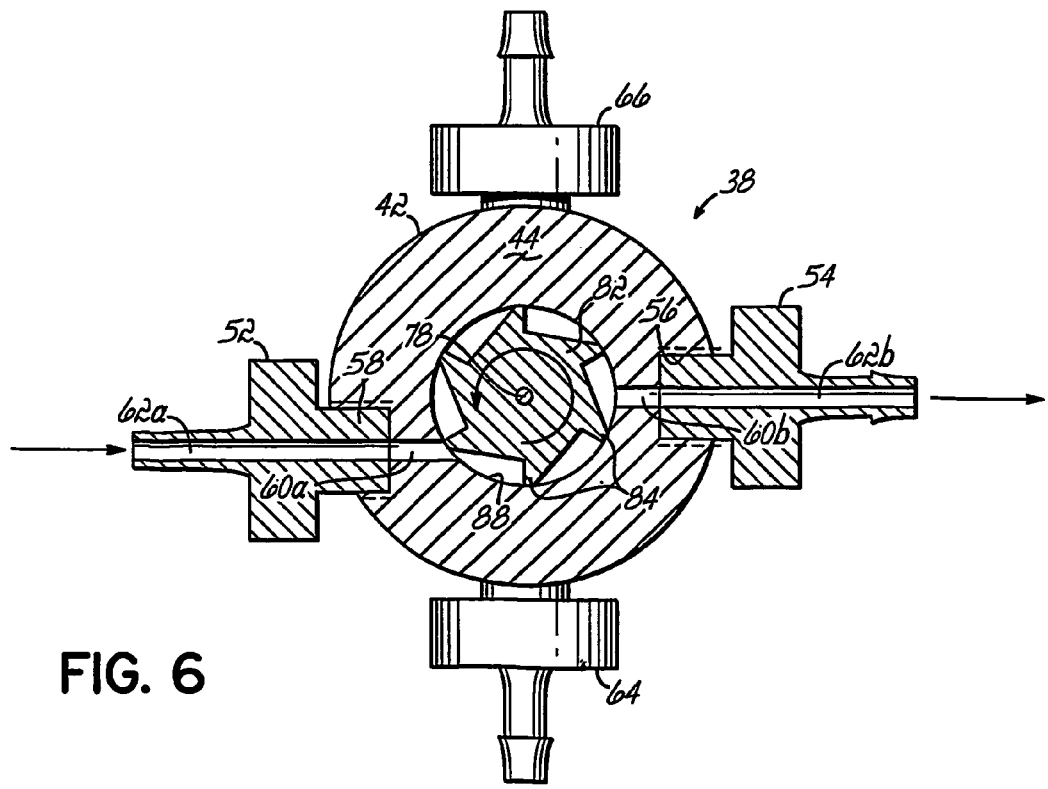
FIG. 6 is a cross sectional view of the processor component of the surge-flow regulator illustrated in FIG. 1 taken along line 6—6 of FIG. 5.

Referring to FIG. 3, processor 38 according to one embodiment of the present invention includes a housing 42 having a body portion 44 and a cap portion 46 mounted to body portion 44 through fasteners 48 and sealed by an annular gasket 50. Body portion 44 of the housing 42 includes an air inlet port 52 connected to a source of pressurized air (not shown) and an air outlet port 54. The body portion 44 includes a pair of threaded bores 56 for receiving threaded nipples 58 of the air inlet and outlet ports 52 and 54. The housing 42 includes a pair of air passages 60a and 60b formed through a wall of the body portion 44 that fluidly communicate with respective air passages 62a and 62b formed in the air inlet and outlet ports 52 and 54, respectively. As shown in FIGS. 5 and 6, air passage 62a of the air inlet port 52 has an axis that is offset from axis of the air passage 62b of the air outlet port 54 that intersects the longitudinal axis of the processor 38.

Referring to FIG. 4, the body portion 44 of housing 42 further includes a fluid inlet port 64 connected to the aspiration line 24 leading from the handpiece 12 and a fluid outlet port 66 connected to the flow limiting device 40 through a portion of the aspiration line 24. The body portion 44 includes a pair of threaded bores 68 for receiving threaded nipples 70 of the fluid inlet and outlet ports 64 and 66. The housing 42 includes a pair of fluid passages 72a and 72b formed through a wall of the body portion 44 that fluidly communicate with respective fluid passages 74a and 74b formed in the fluid inlet and outlet ports 64 and 66, respectively. As shown in FIGS. 5 and 6, the fluid passage 74a of the fluid inlet port 64 is aligned on a common axis with the fluid passage 74b of the fluid outlet port 66 that intersects the longitudinal axis of the processor 38.

A rotatable insert 76 is mounted within the housing 42 through a shaft 78 supported at its opposite ends in a pair of bearings 80. The rotatable insert 76 includes a fan portion 82 mounted to rotate with the shaft 78 and having multiple fan blades 84 that are driven by pressurized air entering the air inlet port 52 and exiting the air outlet port 54. An annular gasket 86 forms a seal with the fan portion 82 and the body portion 44 to create a sealed air chamber 88 within the housing 42 in which the fan blades 84 are free to rotate under the influence of the pressurized air. Rotation of the fan blades 84 under the influence of the pressurized air causes rotation of the shaft 78 mounted to the fan portion 82. It is contemplated that other sources of energy to rotate the fan blades 84 are possible as well without departing from the spirit and scope of the present invention.

As shown in FIGS. 3–5, the rotatable insert 76 further includes multiple cutting blades 90 mounted to rotate with the shaft 78 within a sealed fluid chamber 92 formed by sealing contact of the gasket 50 with the cap portion 46 and the sealing contact of the gasket 86 with the fan portion 82 and the body portion 44. In one embodiment of the present invention, six (6) cutting blades 90 are formed from a disk 94 of material and lie in a plane that is parallel to the axis of the fluid passages 72a and 72b.

In operation of the processor 38 in accordance with the principles of the present invention, fluid and particles of lenticular debris carried by the aspiration line 24 are introduced into the sealed fluid chamber 92. The fan blades 84 are rotated under the influence of pressurized air introduced into the air inlet port 52 to cause the cutting blades 90 to rotate at a selected RPM suitable for the surgical procedure. The cutting blades 90 engage and reduce the sizes of the particles of lenticular debris before the suspension exits the fluid outlet port 66. Other sources of energy to rotate the cutting blades 90 are possible as well without departing from the spirit and scope of the present invention. For example, as shown in FIG. 7, where like numerals represent like parts, the fan portion 82 of the rotatable insert 76 is eliminated, and the shaft 78 is driven by an electrical motor 96 mount d within the housing 42.

In one embodiment of the present invention as shown in FIG. 8, the flow limiting device 40 comprises a lumen 98 placed in fluid communication with the aspiration line 24. The lumen 98 defines a fluid passage 100 having an inner diameter that is less than the inner diameter of the aspiration line 24 through which the fluid and smaller particles of lenticular debris are carried. The reduced inner diameter of the lumen 98 reduces the potential surge inflow of fluid in the aspiration line 24 resulting from an occlusion break at the tip 22. The flow limiting device 40 is interchangeable with flow limiting devices having different lumen sizes. For example, the interchangeable lumens 98 may have an inner diameter ranging from about 0.1 mm$^2$ to about 0.7 mm$^2$. In one embodiment, the lumen 98 is positioned remote from the emulsification tip 22 so the lumen 98 is not influenced by ultrasonic vibration of the tip 22. In an alternative embodiment as shown in FIG. 1, the lumen 98 is positioned remote from the emulsification tip 22 and the handpiece 12 to further isolate the lumen 98 from ultrasonic vibration of the tip 22.

It will be appreciated that processor 38 reduces the sizes of the lenticular debris particles prior to passage of the fluid and debris through the flow limiting device 40. This reduces the chance of clogging the lumen 98 with lenticular debris that may otherwise occlude the lumen 98 and cause a sudden inflow of fluid through the aspiration line 24 during an occlusion break. Mounting of the flow limiting device 40 remote from the emulsification tip 22 reduces the risk of thermal injury to the ocular tissues that could otherwise be caused by prolonged application of ultrasonic energy at the tip 22 to break the occlusion. The interchangeable flow limiting devices 40 having lumens 98 of different inner diameters allows the surgeon to tailor the surge-flow regulator 36 to the surgeon's surgical technique and the particular patient.

A surge-flow regulator 200 in accordance with an alternative embodiment of the present invention is shown in FIGS. 9 and 10 where like numerals represent like parts. In this embodiment, the surge-flow regulator 200 includes a fluid inlet 202 placed in fluid communication with the aspiration line 24 and a flow limiting device 204 mounted at a fluid outlet 206 of the surge-flow regulator 200. The flow limiting device 204 comprises a lumen 208 that defines multiple fluid passages 210a–210d though the lumen 208. A rotatable occluding device 212 is supported by a housing 214 of the surge-flow regulator 200 and includes multiple sets of one or more apertures 216a–216d that communicate with the respective fluid passages 210a–210d of the lumen 208. One set of apertures includes a single aperture 216a, a second set includes apertures 216a–216b, a third set includes apertures 216a–216c and a fourth set includes apertures 216a–216d. The occluding device 212 is selectively rotatable to occlude none, one, two, three or all four of the fluid passages 210a–210d in the lumen 208. As shown in FIG. 9, fluid passages 210a–210b are occluded by occluding device 212. The occluding device 212 allows the surgeon to tailor the surge-flow regulator 200 to the surgeon's surgical technique and the particular patient. It is contemplated that the number of fluid passages 210a–210d can be changed, and the particular inner diameter of each fluid passage 210a–210d can be chosen for a particular surgical procedure.

Further referring to FIG. 9, the surge-flow regulator 200 includes a processor 218 placed in fluid communication with the aspiration line 24 and upstream of the lumen 208 to reduce the sizes of the lenticular debris particles carried through the aspiration line 24 before the fluid and particles are introduced to the flow limiting device 204. In this embodiment, the processor 218 comprises multiple cutting blades 220 mounted to rotate with a shaft 222. The shaft 222 is driven by a motor (not shown) or any other suitable energy source that is capable of rotating the shaft 222 and cutting blades 220 at the required RPM for the surgical procedure.

Referring now to FIG. 11, a surge-flow regulator 300 in accordance with another alternative embodiment is shown, where like numerals represent like parts. In this embodiment, the surge-regulator 300 comprises a phacoemulsification rod 302 positioned within the aspiration line 24 to emulsify the lenticular debris as it carried in the aspiration line 24 and a flow limiting device 304. The flow limiting device 304 is in the form of an iris member 306 having a variable inner diameter, and is placed in fluid communication with the aspiration line 24 and downstream of the rod 302. The rod 302 reduces the sizes of the lenticular debris particles carried through the aspiration line 24 before the fluid and particles are introduced to the flow limiting device 304. The inner diameter of the iris member 306 may be manually or automatically controlled.

An alternative surge-flow regulator 400 is shown in FIG. 12 in accordance with principles of the present invention, where like numerals represent like parts. In this embodiment, the surge-regulator 400 comprises multiple rotating cutting teeth 402 positioned within the aspiration line 24 to reduce the sizes of the lenticular debris particles carried through the aspiration line 24 before the fluid and particles are introduced to a flow limiting device 404. The cutting teeth 402 are mounted on a gear ring 406 that is driven by a motor 408. The flow limiting device 404 is in the form of an iris member 410 having a variable inner diameter, and is placed in fluid communication with the aspiration line 24 and downstream of the cutting teeth 402.

Referring now to FIGS. 13, 14 and 15A–15E, a flow limiting device 500 in accordance with an alternative embodiment of present invention is shown. In this embodiment, the flow limiting device 500 is mounted externally to the aspiration line 24 and includes a pair of compression members 502a and 502b adapted to apply external pressures to the aspiration line 24 at spaced apart locations that define a pair of spaced apart fluid passages 504a and 504b (FIG. 15B) within the aspiration line 24. The spaced apart fluid passages 504a and 504b within the aspiration line 24 have respective diameters that change upon changing the external pressures applied to the aspiration line 24 by the pair of compression members 502a and 502b.

The flow limiting device 500 includes a base member 506 joined to an upper plate member 508 through fasteners 510 so that the base plate member 506 and upper plate member 508 are fixed relative to each other and the aspiration conduit 24 extends between the fasteners 510 as shown in FIG. 14. A shuttle member 512 having a pair of elongated slots 514 is mounted between the upper plate member 508 and the pair of compression members 502a and 502b. The pair of compression members 502a and 502b are biased upwardly toward the shuttle member 512 by springs 516.

In use, the flow limiting device 500 is clamped about the aspiration line 24 so that the pair of compression members 502a and 502b are positioned to apply external pressures to the aspiration conduit 24 at spaced apart locations. The shuttle member 512 is connected to a piston or other type of actuator that is operable to reciprocate the shuttle member 512 relative to the fixed base plate member 506 and upper plate member 508. The fasteners 510 extend through the elongated slots 514 formed in the shuttle member 512 so that the fasteners 510 are free to travel in the slots 514 during reciprocating movement of the shuttle member 512.

The shuttle member 512 has a pair of opposite cam surfaces 518a and 518b that cooperate with the pair of compression members 502a and 502b so that during one stroke of the shuttle member 512 in one direction (i.e., to the left as shown in FIG. 13), cam surface 518a forces the compression member 502a toward the base plate member 506 so that an external pressure is applied to the aspiration line 24 that defines the fluid passage 504a (FIG. 15A) within the aspiration line 24. The reduced diameter of fluid passage 504a limits post occlusion surge inflow of fluid in the aspiration line 24 following an occlusion break at the tip 22. The other compression member 502b is biased upwardly by the springs 516 in this position of the shuttle member 512 so it does not apply an external pressure to the aspiration line 24 at the spaced apart location.

Referring to FIG. 15B, as the shuttle member 512 is reciprocated in the opposite direction (i.e., to the right as shown in FIG. 13), the cam surfaces 518a and 518b force both compression members 502a and 502b toward the base plate member 506 so that external pressures are applied to the aspiration line 24 at spaced apart locations that define the pair of spaced apart fluid passages 504a and 504b (FIG. 15B) within the aspiration line 24.

Continued movement of the shuttle member 512 to its full stroke in the opposite direction (i.e., to the right as shown in FIG. 13) results in the cam surface 518b maintaining a force applied to compression member 502b so that an external pressure maintains the fluid passage 504b (FIG. 15C) within the aspiration line 24. The other compression member 502a is biased upwardly by the springs 516 in this position of the shuttle member 512 so it does not apply an external pressure to the aspiration line 24 at the spaced apart location. FIGS. 15D and 15E illustrate movement of the compression member 512 back in the direction described in connection with FIG. 15A. During the entire full stroke of the shuttle member 512 in each opposite direction, the aspiration line 24 has a reduced inner diameter either at fluid passage 504a, fluid passage 504b, or at both fluid passages, so that the reduced diameter of the aspiration line 24 limits post occlusion surge inflow of fluid in the aspiration line 24 following an occlusion break at the tip 22 yet debris is allowed to pass through the aspiration line 24 to the receptacle (not shown) of the phacoemulsification machine 14. The shuttle member 512 may be actuated at a rapid rate, such as about 400 cycles per minute.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A surge-flow regulator for use with an ophthalmic surgical instrument having an infusion line adapted to irrigate a surgical site with a fluid and an aspiration line adapted to carry the fluid and particles of lenticular debris away from the surgical site, comprising:
    a processor adapted to be placed in fluid communication with the aspiration line and operable to process the particles of lenticular debris carried in the aspiration line with the fluid into smaller particles; and
    a flow limiting device adapted to be placed in fluid communication with the aspiration line and positioned downstream of the processor, the flow limiting device defining a fluid passage having an inner diameter that is less than an inner diameter of the aspiration line through which the fluid and smaller particles of lenticular debris are carried to thereby control surge-flow of the fluid and lenticular debris through the aspiration line.

2. The surge-flow regulator of claim 1 wherein the flow limiting device comprises a lumen adapted to be placed in fluid communication with the aspiration line.

3. The surge-flow regulator of claim 2 wherein the lumen is interchangeable with a lumen having a different inner diameter.

4. The surge-flow regulator of claim 1 wherein the flow limiting device comprises an adjustable iris device adapted to be placed in fluid communication with the aspiration line that defines a fluid passage having a variable inner diameter.

5. The surge-flow regulator of claim 1 wherein the flow limiting device comprises a lumen adapted to be placed in fluid communication with the aspiration line that defines a plurality of fluid passages therethrough.

6. The surge-flow regulator of claim 5 further comprising a flow occluding device operatively coupled to the lumen for selectively occluding one or more of the plurality of fluid passages.

7. The surge-flow regulator of claim 1 wherein the processor comprises a rotating blade.

8. The surge-flow regulator of claim 1 wherein the processor comprises a phacoemulsification rod.

9. A surge-flow regulator for use with an ophthalmic surgical instrument having an elongated handpiece containing an infusion line adapted to irrigate a surgical site with a fluid and an emulsification tip in fluid communication with an aspiration line adapted to carry the fluid and particles of emulsified lenticular debris away from the surgical site, comprising:
    a flow limiting device adapted to be placed in fluid communication with the aspiration line and positioned remote from the emulsification tip, the flow limiting device defining a fluid passage having an inner diameter that is continuously less than an inner diameter of the aspiration line, independent of pressure within the aspiration line, through which the fluid and particles of lenticular debris are carried to thereby control surge-flow of the fluid and lenticular debris through the aspiration line.

10. The surge-flow regulator of claim 9 wherein the flow limiting device is adapted to be positioned remote from the handpiece.

11. The surge-flow regulator of claim 9 wherein the flow limiting device comprises a lumen adapted to be placed in fluid communication with the aspiration line.

12. The surge-flow regulator of claim 11 wherein the lumen is interchangeable with a lumen having a different inner diameter.

13. The surge-flow regulator of claim 9 wherein the flow limiting device comprises an adjustable iris device adapted to be placed in fluid communication with the aspiration line that defines a fluid passage having a variable inner diameter.

14. The surge-flow regulator of claim 9 wherein the flow limiting device comprises a lumen adapted to be placed in fluid communication with the aspiration line that defines a plurality of fluid passages therethrough.

15. The surge-flow regulator of claim 14 further comprising a flow occluding device operatively coupled to the lumen for selectively occluding one or more of the plurality of fluid passages.

16. A surge-flow regulator for use with an ophthalmic surgical instrument having an infusion line adapted to irrigate a surgical site with a fluid and an aspiration line adapted to carry the fluid and particles of lenticular debris away from the surgical site, comprising:
a flow limiting device, independent of the infusion line, adapted to be operatively connected externally to the aspiration line and operable to apply external pressures thereto at spaced apart locations that define a pair of fluid passages within the aspiration line having respective inner diameters that change upon changing the external pressures applied to the aspiration line by the flow limiting device to thereby control surge-flow of the fluid and lenticular debris through the aspiration line.

17. The flow limiting device of claim 16 wherein the flow limiting device comprises a pair of members adapted to apply the external pressures to the aspiration line at the spaced apart locations to define the pair of spaced apart fluid passages within the aspiration line.

18. An ophthalmic surgical system having an elongated handpiece containing an infusion line adapted to irrigate a surgical site with a fluid and an emulsification tip in fluid communication with an aspiration line adapted to carry the fluid and particles of emulsified lenticular debris away from the surgical site, comprising:
a flow limiting device in fluid communication with the aspiration line and positioned remote from the emulsification tip, the flow limiting device defining a fluid passage having an inner diameter that is continuously less than an inner diameter of the aspiration line, independent of pressure within the aspiration line, through which the fluid and particles of lenticular debris are carried to thereby control surge-flow of the fluid and lenticular debris through the aspiration line.

19. The ophthalmic surgical instrument of claim 18 further comprising a processor in fluid communication with the aspiration line and positioned upstream of the flow limiting device, the processor being operable to process the particles of lenticular debris carried in the aspiration line with the fluid into smaller particles prior to passage through the fluid passage.

20. The ophthalmic surgical instrument of claim 19 wherein the processor comprises a rotating blade.

21. The ophthalmic surgical instrument of claim 19 wherein the processor comprises a phacoemulsification rod.

22. The ophthalmic surgical instrument of claim 18 wherein the flow limiting device comprises a lumen placed in fluid communication with the aspiration line.

23. The ophthalmic surgical instrument of claim 22 wherein the lumen is interchangeable with a lumen having a different inner diameter.

24. The ophthalmic surgical instrument of claim 18 wherein the flow limiting device comprises an adjustable iris device placed in fluid communication with the aspiration line that defines a fluid passage having a variable inner diameter.

25. The ophthalmic surgical instrument of claim 18 wherein the flow limiting device comprises a lumen placed in fluid communication with the aspiration line that defines a plurality of fluid passages therethrough.

26. The ophthalmic surgical instrument of claim 25 further comprising a flow occluding device operatively coupled to the lumen for selectively occluding one or more of the plurality of fluid passages.

* * * * *